US00PP34794P2

(12) United States Plant Patent
Clark et al.

(10) Patent No.: US PP34,794 P2
(45) Date of Patent: Dec. 6, 2022

(54) GRAPEVINE PLANT NAMED 'CLARION'

(50) Latin Name: ***Vitis* spp. hybrid**
Varietal Denomination: Clarion

(71) Applicant: Regents of the University of Minnesota, Minneapolis, MN (US)

(72) Inventors: Matthew D. Clark, Hopkins, MN (US); James Luby, St. Paul, MN (US); Peter Hemstad, Edina, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 17/590,855

(22) Filed: Feb. 2, 2022

Related U.S. Application Data

(60) Provisional application No. 63/145,447, filed on Feb. 3, 2021.

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./207
CPC ..... A01H 5/08; A01H 5/00; A01H 6/88
See application file for complete search history.

(56) References Cited

U.S. PATENT DOCUMENTS

PP14,617 P3 * 3/2004 Luby ..... A01H 6/88
Plt./207

OTHER PUBLICATIONS van Zoeren et al. Grape Selection From the VivisGen and VitisGen2 Projects, The Grapevine Magazine retrieved on Apr. 25, 2022 at https://thegrapevinemagazine.net/2021/04/grape-selections-from-the-vitisgen-and-vitisgen2-projects/, 10 pp. (Year: 2021).*

* cited by examiner

*Primary Examiner* — June Hwu
(74) *Attorney, Agent, or Firm* — Penny J. Aguirre

(57) ABSTRACT

The invention is a new and distinct variety of grapevine plant named 'Clarion' that is characterized by its grapes with a moderate juice total acidity (average of 7.73 g/L) making it suitable for wine production, its grapes that lack less desirable aromatic compounds that are typical of cold climate hybrid grapes, its grapes with floral notes including lilac and tropical fruit notes, its good growth habit without excessive vigor, and its grapes with a loose cluster architecture.

1 Drawing Sheet

STATEMENT REGARDING FEDERALLY SPONSORED RESEARCH

This invention was made with government support under 2017-51181-26829 and 2011-51181-30635 awarded by a Specialty Crop Research Initiative Competitive Grant. The government has certain rights in the invention.

Botanical classification: *Vitis* spp. hybrid.
Variety denomination: 'Clarion'.

BACKGROUND OF THE INVENTION

The present invention relates to a new and distinct cultivar of grape plant botanically known as *Vitis* spp. hybrid 'Clarion', referred to hereafter by its cultivar name, 'Clarion'.

'Clarion' resulted from an ongoing research program in Excelsior, Minn. with the objective of the breeding program to develop new cultivars of cold-hardy grapes suitable for grape production in the Eastern United States. 'Clarion' originated from a cross made in June of 1992 between the *Vitis* spp. hybrid cultivar 'VB 86-4' (not patented) as the female parent and 'Frontenac' (not patented) as the male parent. 'Clarion' was selected as a single unique plant from the seedlings that derived from the above cross in 1998.

Asexual propagation of the new cultivar was first accomplished by hardwood stem cuttings in 2009 by the Inventors at a research center near Excelsior, Minn. Asexual propagation of the new cultivar by hardwood stem cuttings and tissue culture using meristamic tissue has determined that the characteristics are stable and true to type in successive generations.

SUMMARY OF THE INVENTION

The following traits have been repeatedly observed and represent the characteristics of the new cultivar. These attributes in combination distinguish 'Clarion' as a new and unique cultivar of *Vitis*.

1. 'Clarion' exhibits grapes with a moderate juice total acidity (average of 7.73 g/L) making it suitable for wine production.
2. 'Clarion' exhibits grapes that lack less desirable aromatic compounds that are typical of cold climate hybrid grapes.
3. 'Clarion' exhibits grapes with floral notes including lilac and tropical fruit notes.
4. 'Clarion' exhibits a good growth habit without excessive vigor.

5. 'Clarion' exhibits grapes with a loose cluster architecture.

'VB 86-4', the female parent plant of 'Clarion', differs from 'Clarion' in having grapes that are larger in size and in having less cold hardiness. 'Frontenac', the male parent of 'Clarion', differs from 'Clarion' in having grapes that are black in color with a higher juice total acidity (average of 13.4 g/L) and in being less cold-hardy. 'Clarion' can also be compared to the *Vitis* cultivars 'Itasca' (U.S. Plant Pat. No. 29,847) and 'La Crescent' (U.S. Plant Pat. No. 14,617). 'Itasca' is similar to 'Clarion' in having grapes that are similar in color, have a low total acidity, and similar sugar content at harvest. 'Itasca' differs from 'Clarion' in being more cold-hardy and in having grapes that are smaller in size a harvest date that is earlier. 'La Crescent' is similar to 'Clarion' in having grapes with similar cluster and berry weights and harvest date. 'La Crescent' differs from 'Clarion' in having grapes with more berry shelling, less even ripening within clusters, and a lower sugar content.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures related to research trials without any offers for sale include website listings by American Society for Horticultural Science, USDA REEIS, Iowa State University, University of Minnesota, Midwest Winepress, University of Wisconsin, American Journal of Enology and Viticulture.

BRIEF DESCRIPTION OF THE DRAWING

The accompanying color photograph represent typical mature berry clusters on vines of 'Clarion' as grown under standard field conditions in Excelsior, Minn. The photograph was taken of a grapevine 20 years in age and provides a view of a vine in fruit of 'Clarion'. The colors in the photograph is as close as possible with the photographic and printing technology utilized and the values cited in the detailed botanical description accurately describe the colors of the new grapevine.

DETAILED BOTANICAL DESCRIPTION

The following traits have been repeatedly observed and represent the characteristics of the new cultivar. The measurements, observations and descriptions that follow describe a plant 20 years in age as grown outdoors in a trial vineyard in Excelsior, Minn. with detailed botanical data collected during the 2015 to 2019 growing seasons. 'Clarion' has not been observed under all possible environmental conditions and the phenotype may vary somewhat with variations in temperature, day length, light intensity, soil types and water and fertility levels, pruning, pest control and other cultural practices without, however, any variance in the genotype.

Many of the descriptors are based on those set forth by the International Board for Plant Genetic Resources in collaboration with the Office Internationale de la Vigne et du Vin (OIV) and the International Union for the Protection of New Varieties of Plants. All dimensions are given as means. The color determination is in accordance with The 2015 R.H.S. Colour Chart of The Royal Horticultural Society, London, England, except where general color terms of ordinary dictionary significance are used.

General description:

*Blooming period.*—Typically first two weeks of June.
*Plant type.*—Perennial fruit producing vine.
*Plant habit.*—Open and orderly.
*Propagation.*—Hardwood stem cuttings.
*Growth rate.*—Moderately vigorous.

Mature canes:

*Color of canes.*—One-year-old canes; a blend of 175A, 165B and 166A, new canes; 144D, blend of 178A, 166A and 174A.
*Length of canes.*—One-year-old canes; average of 1.8 m (prior to pruning).
*Diameter of canes.*—Average of 6.5 mm mid cane.
*Diameter at nodes.*—Average of 8.3 mm.
*Internode length.*—Average of 7.5 mm.
*Lenticels.*—Dormant cane; Average of 1.2 mm in length and 1 mm width, round to oblong in shape, 200A and 201A in color, 15 per area 5 mm in width and 1 cm in length, new cane; 12 to 15 with 30 unformed per area 5 mm in width and 1 cm in length with same characteristics as mature cane.
*Cane cross-section shape.*—Oval to round.
*Surface.*—Smooth with no hairs.
*Density of hairs on mature cane.*—None.
*Tendril pattern on shoot.*—2,0,2,0 etc. (two nodes with a tendril followed by one node without).
*Tendrils forked.*—Yes.
*Tendril texture.*—Glabrous.
*Tendril length.*—5.5 to 12 cm in length, 1.5 to 2 mm in diameter.
*Tendril color.*—Young shoots 144A, mature 166A.
*Bud width.*—4 mm.
*Bud length.*—6 mm.
*Bud shape.*—Triangular.
*Bud color.*—A blend of 165A and 165B.
*Bud burst.*—Medium.

Trunk:

*Bark texture.*—Flaky, vertical segments up to 2 cm in length and 4 mm in width.
*Bark color.*—Striated, 165A, a blend of 202A and 201A, and 200D.
*Trunk shape.*—Oval.
*Trunk diameter.*—An average of 3.5 cm on diameter measured 20 cm above soil on 6 year-old-trunk.

Mature leaves: Descriptors including the designations N1 through N5, relate to "OIV—Code Numbers 065-093" of *Preliminary Minimal Descriptor List for Grapevine Varieties* (Dettweiler E., 1991, Institut fur Rebenzüchtung, Geilweilerhof, Germany).

*Length of blade.*—14 cm.
*Width of blade.*—13 cm.
*Shape of blade.*—Fig-like.
*Number of lobes.*—5.
*Blade margins.*—Incised into lobes with lobes moderately to deeply serrated.
*Length of primary (midrib) vein n1 from the tip of the blade to the petiole sinus.*—10 cm.

*Length of petiole compared to length of middle vein (midrib).*—Middle vein is 1.5 cm longer than length of petiole.

*Length of vein n2 from the tip of the first major lobe of the blade to the petiole sinus.*—9 cm.

*Length of vein n3 from the tip of the second major lobe of the blade to the petiole sinus.*—7.7 cm.

*Length of vein n4 from the tip of the third major lobe of the blade to where it joins the vein measured in n3.*—6 cm.

*Length of vein n5 from the tip of the first tooth proximal to the petiole sinus to where it joins the vein measured in n4.*—4 cm.

*Leaf vein anthocyanin.*—None.

*Density of erect hairs between the leaf veins on lower leaf surface.*—Absent.

*Length of n2 teeth.*—Up to 1 cm.

*Width of n2 teeth.*—Up to 1.7 cm.

*Length/width ratio of n2 teeth.*—1.38 cm.

*Length of n4 teeth.*—1.2 cm.

*Width of n4 teeth.*—1.2 cm.

*Length/width ratio of n4 teeth.*—1 cm.

*Shape of teeth.*—Convex.

*Arrangement of petiolar sinus.*—Wide open.

*Shape of petiolar sinus.*—Wide open.

*Shape of base of petiolar sinus.*—Lyre-shaped.

*Depth of petiolar sinus.*—4 cm.

*Width of petiolar sinus.*—1 cm.

*Petiole.*—7 cm in length, 2 mm in width, 144B in color and suffused with 183A on sun exposed side.

*Shape of upper sinuses.*—Urn-shaped.

*Shape of base of upper sinuses.*—Rounded.

*Arrangement of upper sinuses.*—Wide open.

*Glossiness of adaxial and abaxial surface.*—Adaxial surface is glossy and abaxial surface is not and has low density of small, intervenal trichomes.

*Pubescence on adaxial surface.*—None.

*Pubescence on abaxial surface.*—Very minute erect hairs on veins.

*Blistering on adaxial surface.*—None.

*Color of adaxial leaf surface.*—137B, veins 145A.

*Color of abaxial leaf surface.*—138B, veins 145A.

*Color of leaf petiole.*—144D blend of 166A, 175A, and 178A.

*Center lobe size.*—6 cm in length and width.

*Lateral lobe size.*—5.5 cm in length and width.

*Basal lobe size.*—5 cm in length and width.

*Density of foliage.*—Moderate.

Young shoots:

*Form of shoot tip.*—Mainly open.

*Density of prostate hairs on tip.*—Moderately pubescent.

*Anthocyanin coloration of the prostrate hairs on tip.*—Absent or very weak.

*Density of erect hairs on tip.*—None observed.

*Petiole pigmentation.*—A blend of 145A, and 145C and striated and suffused with 183A, B on sun exposed side.

*Shoot attitude.*—Semi-erect.

*Shoot pigmentation (internodes and nodes).*—A blend of 145A and 145B and striated and suffused with 183B on the dorsal side and a blend of 145A and 145B with very slight hints of 183B on the ventral side.

*Young leaves.*—144C in color on upper surface, 144B on lower surface, upper surface glossy, lower surface matte, veins match surface colors.

Flowers:

*Fragrance.*—Moderately fragrant.

*Mean time of flowering.*—June 11 when grown in Excelsior, Minn.

*Color of calyx.*—144A.

*Flowering shoot vigor.*—Vigorous.

*Flowering shoot attitude.*—Semi-erect to erect

*Sepal number.*—5, sepals fused into continuous calyx.

*Calyx shape.*—Ring-shaped.

*Calyx size.*—<1 mm in length, 2 mm in width.

*Calyx apex.*—Fused to ovary.

*Calyx base.*—Fused to pedicel.

*Nectary.*—1.5 mm in diameter, <1 mm in length, N144A in color.

*Calyx surface.*—Glabrous.

*Petals.*—5 to 6, fused in calyptra cohering at summit; 2.5 mm in width and 1 mm in depth and separating at base; 3.8 mm in width, 2.2 mm in depth; reflexed after dehiscence, 144A in color, margins slightly transluscent and 155B in color.

*Shape of cluster.*—Conical.

*Size of cluster.*—10 cm in length, 2.5 cm at base (3 mm at mid section).

*Number of flowers/cluster.*—Average of 150 and up to 65 on wings if present.

*No. of clusters per cane.*—Average of 2.

*Flower buds.*—4 mm in length, 2 mm in width, 144B in color, obovate in shape, glabrous and slightly glossy surface.

*Size of individual entire flower.*—4 mm in height, 1.1 cm in width (to end of stamens).

*Pollen fertility.*—Fertile based on use in controlled crosses.

*Reproductive organs.*—Fully developed stamens and fully developed gynoecium.

*Color of stamen.*—Anther: 160C, Filament: NN155C.

*Stamen number.*—Average of 5 to 6.

*Filament length.*—3.02 to 3.84 mm.

*Anther.*—1.08 to 1.14 mm in length.

*Pollen quantity and color.*—Abundant and 15D in color.

*Pistil.*—1, ovary is 1.5 mm in length and 1 mm in width at base, urn-shaped, glabrous surface color 144B, stigma 1 mm in width and <1 mm in length, color a blend between 20B and 144B.

*Pedicel.*—2.11 to 2.89 mm in length and <1 mm in width, surface glabrous, color 144A.

*Peduncle.*—1 cm in length, 1 mm in width, 144A in color, glabrous surface.

*Position of first flowering and fruiting node.*—Typically node 3.

Fruit:

*Cluster length.*—Average of 15.5 cm (ranges from 14 to 19 cm).

*Cluster shoulders.*—Typically 1 (rarely 2).

*Cluster diameter.*—Average of 9 cm (ranges from 7 to 10 cm).

*Cluster weight.*—119.8 g (ranges from 92.0 to 150.3).

*Cluster density.*—Medium to very dense, average of 102 berries per cluster.

*Berry weight.*—1.65 g (ranges from 1.16 to 1.77 g).

*Berry length.*—Average of 1.4 cm.

*Berry diameter at equator*.—Average of 1.4 cm.
*Berry shape*.—Round.
*Berry cross-section*.—Circular.
*Berry, color of skin*.—Just before maturity; 144B tinged with 152C, at maturity; 152B, suffused with 166B with moderate bloom of 201D.
*Berry, color of flesh*.—165C with slight tinge of 147C with very weak or no anthocyanin presence.
*Berry firmness*.—Very firm.
*Berry skin thickness*.—Moderate.
*Berry skin bloom* (*cuticular wax*).—Moderate to heavy.
*Berry size uniformity*.—Medium.
*Berry, particular flavor*.—Neutral, not strongly aromatic.
*Length of pedicel*.—6 mm.
*Pedicel diameter*.—1.4 mm (3 mm at base).
*Pedicel color*.—A color between 160A and N144A.
*Peduncle* (*rachis*).—An average of 14 cm in length and 3 mm in width (mid point), a blend of 160A and N144A with some anthocyanin shading of 174A.
*Berry, separation from pedicel*.—Difficult.
*Berry, presence of seeds*.—Fully developed.
*Seed number/berry*.—3.
*Seed length*.—5.5 mm.
*Seed width*.—3.5 mm.
*Seed length/width ratio*.—1.57.
*Seed weight*.—0.04 g.
*Seed color*.—A blend of 200C and 161A.

Fruit chemistry and harvest: Values represent the means (with ranges in parentheses) for fruit harvested over five growing seasons 2015-2019.

*Harvest date*.—September 25 (September 19-October 9).
*Time of beginning berry ripening*.—First week of August.
*Brix*.—23.84 (21.7-24.5).
*Ph*.—3.186 (3.12-3.28).
*Titratable acidity*.—7.73 (5.50-8.36) g/L.
*Malate*.—3.7 g/L.
*Berry use*.—Wine production.
*Berry storage*.—Not applicable, used directly for wine making at harvest.

Vineyard performance: Based on observations compiled over five years (2015-2019).

*Susceptibility to powdery mildew* (*uncinula necator*).—Moderate.
*Susceptibility to downy mildew* (*plasmopara viticola*).—None.
*Susceptibility to black rot* (*guignardia bidwellii*).—Moderate to high.
*Susceptibility to grey mold* (*botrytis cinerea*).—None.
*Susceptibility to foliar phylloxera* (*daktulosphaira vitifoliae*).—Moderate.
*Susceptibility to crown gall* (*agrobacterium tumefaciens*).—None.
*Susceptibility to phenoxy herbicide drift* (*e.g.*, 2,4-*d*).—None.
*Berry splitting*.—None.
*Berry shelling*.—Low.
*Vigor level*.—High.
*Cold hardiness*.—At least in U.S.D.A. Zone 5, low to moderate in U.S.D.A. Zone 4.
*Wood ripening*.—Good.

It is claimed:

1. A new and distinct variety of grapevine plant named 'Clarion' as described and illustrated herein.

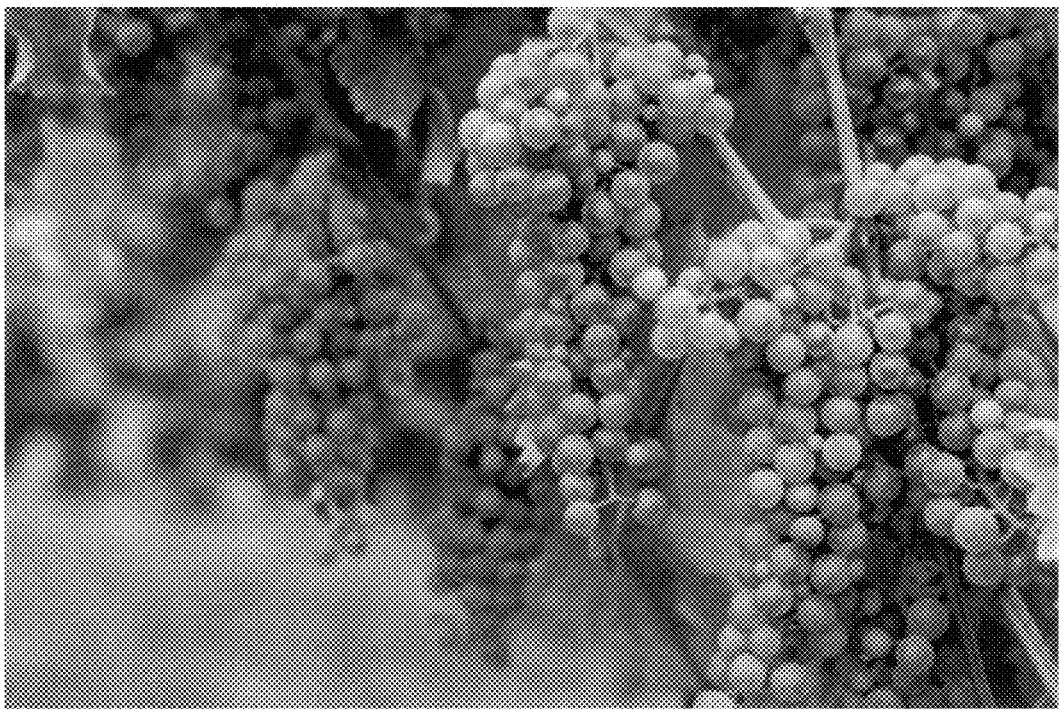

* * * * *